United States Patent
Engel et al.

(10) Patent No.: US 12,378,324 B2
(45) Date of Patent: Aug. 5, 2025

(54) ANTI SUPEROXIDE DISMUTASE 1 (SOD1) ANTIBODIES AND USE THEREOF

(71) Applicant: B. G. NEGEV TECHNOLOGIES AND APPLICATIONS LTD., AT BEN-GURION UNIVERSITY, Beer Sheva (IL)

(72) Inventors: Stanislav Engel, Beer Sheva (IL); Zeev Barak, Beer Sheva (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 1107 days.

(21) Appl. No.: 17/297,167

(22) PCT Filed: Nov. 28, 2019

(86) PCT No.: PCT/IL2019/051307
§ 371 (c)(1),
(2) Date: May 26, 2021

(87) PCT Pub. No.: WO2020/110122
PCT Pub. Date: Jun. 4, 2020

(65) Prior Publication Data
US 2022/0025068 A1 Jan. 27, 2022

Related U.S. Application Data

(60) Provisional application No. 62/772,224, filed on Nov. 28, 2018.

(51) Int. Cl.
*C07K 16/40* (2006.01)
*G01N 33/573* (2006.01)

(52) U.S. Cl.
CPC .......... *C07K 16/40* (2013.01); *G01N 33/573* (2013.01); *C07K 2317/24* (2013.01); *C07K 2317/34* (2013.01); *C07K 2317/622* (2013.01); *C07K 2317/76* (2013.01); *G01N 2333/90283* (2013.01); *G01N 2800/2835* (2013.01)

(58) Field of Classification Search
CPC .......... C07K 2317/24; C07K 2317/34; C07K 2317/622; C07K 2317/76; G01N 2333/90283; G01N 2800/2835
See application file for complete search history.

(56) References Cited

U.S. PATENT DOCUMENTS

2008/0206251 A1   8/2008  Cashman et al.

FOREIGN PATENT DOCUMENTS

| WO | 2012058220 A2 | 5/2012 | |
|---|---|---|---|
| WO | 2012080518 A1 | 6/2012 | |
| WO | WO-2015156268 A1 * | 10/2015 | ........... A61K 39/395 |
| WO | WO-2016047652 A1 * | 3/2016 | ................ A61P 7/04 |
| WO | 2017115367 A1 | 7/2017 | |

OTHER PUBLICATIONS

Cleveland Clinic, Amyotrophic Lateral Sclerosis (ALS), 2024, retrieved from: https://my.clevelandclinic.org/health/diseases/16729-amyotrophic-lateral-sclerosis-als (Year: 2024).*

Nih, Amyotrophic Lateral Sclerosis (ALS), 2024, retrieved from: https://www.ninds.nih.gov/health-information/disorders/amyotrophic-lateral-sclerosis-als (Year: 2024).*

Gros-Louis et al., Intracerebroventricular infusion of monoclonal antibody or its derived Fab fragment against misfolded forms of SOD1 mutant delays mortality in a mouse model of ALS, 2010, Journal of Neurochemistry, vol. 113, pp. 1188-1199 (Year: 2010).*

Broering et al., Identification of Human Monoclonal Antibodies Specific for Human SOD1 Recognizing Distinct Epitopes and Forms of SOD1, 2013, PLOS One, vol. 8, Issue 4, pp. 1-13 (Year: 2013).*

Zhu et al., Pathological insights from amyotrophic lateral sclerosis animal models: comparisons limitations, and challenges, 2023, Translational Neurodegeneration, vol. 12, Issue 46, pp. 1-16 (Year: 2023).*

DiBernardo et al., Translating preclinical insights into effective human trials in ALS, 2006, Biochimica et Biophysica Acta, pp. 1139-1149 (Year: 2006).*

Marcel Maier et al., "A human-derived antibody targets misfolded SOD1 and ameliorates motor symptoms in mouse models of amyotrophic lateral sclerosis", Sci Transl Med. Dec. 5, 2018;10(470):eaah3924.

Victor Banerjee et al. "Superoxide Dismutase 1 (SOD1)-Derived Peptide Inhibits Amyloid Aggregation of Familial Amyotrophic Lateral Sclerosis SOD1 Mutants", ACS Chem Neurosci., Nov. 2016, 16;7(11):1595-1606.

Jacob I Ayers et al, "Experimental transmissibility of mutant SOD1 motor neuron disease", Acta Neuropathol., Dec. 2014;128(6):791-803.

(Continued)

*Primary Examiner* — Jeffrey Stucker
*Assistant Examiner* — Brittney E Donoghue
(74) *Attorney, Agent, or Firm* — The Roy Gross Law Firm, LLC; Roy D. Gross

(57) ABSTRACT

The present invention is directed to an antibody or an antigen-binding portion thereof having specific binding affinity to a misfolded SOD1. Pharmaceutical compositions comprising same and methods of using same are also provided.

17 Claims, 2 Drawing Sheets
Specification includes a Sequence Listing.

(56) References Cited

OTHER PUBLICATIONS

Munch, C., O'Brien, J. & Bertolotti, A. "Prion-like propagation of mutant superoxide dismutase-1 misfolding in neuronal cells", Proc. Natl. Acad. Sci., Mar. 2011, vol. 108;9, 3548-3553, (2011).
Hsueh-Ning Liu et al., "Targeting of monomer/misfolded SOD1 as a therapeutic strategy for amyotrophic lateral sclerosis", J Neurosci. Jun. 27, 2012;32(26):8791-9.
Urushitani, M., Sik, A., Sakurai, T. et al. "Chromogranin-mediated secretion of mutant superoxide dismutase proteins linked to amyotrophic lateral sclerosis". Nat Neurosci 9, 108-118 (2006).
Bradley J. Turner et al., "Impaired Extracellular Secretion of Mutant Superoxide Dismutase 1 Associates with Neurotoxicity in Familial Amyotrophic Lateral Sclerosis", Journal of Neuroscience, Jan. 5, 2005, 25 (1) 108-117.
Makoto Urushitani et al., "Therapeutic effects of immunization with mutant superoxide dismutase in mice models of amyotrophic lateral sclerosis", Proc Natl Acad Sci U S A. Feb. 13, 2007; 104(7): 2495-2500.
Francois Gros-Louis et al, "Intracerebroventricular infusion of monoclonal antibody or its derived Fab fragment against misfolded forms of SOD1 mutant delays mortality in a mouse model of ALS", J Neurochem. Jun. 2010;113(5):1188-99.
PCT Search Report for International Patent Application No. PCT/IL2019/051307, mailed Feb. 17, 2020, 7 pp.
PCT Written Opinion for International Patent Application No. PCT/IL2019/051307, mailed Feb. 17, 2020, 6 pp.

\* cited by examiner

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Asp Ser Ala Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Ile Asn Thr Tyr Thr Gly Lys Pro Thr Tyr Ala Asp Asp Phe Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Ser Val Tyr Ser Tyr Asp Gly Thr Phe Tyr Arg Tyr Phe Leu Asp Ala
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Ala Ser Glu Ser Val Ser Lys His Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Leu Ala Ser Ser Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Ser Trp Asn Asp Pro Trp Thr
1               5

<210> SEQ ID NO 7
<211> LENGTH: 145
<212> TYPE: PRT
<213> ORGANISM: Artificial Sequence
<220> FEATURE:
<223> OTHER INFORMATION: Synthetic

<400> SEQUENCE: 7

Met Asp Trp Val Trp Asn Leu Leu Phe Leu Met Ala Val Ala Gln Thr
1               5                   10                  15

Gly Ala Gln Ala Gln Ile Gln Leu Val Gln Ser Gly Pro Glu Leu Lys
            20                  25                  30

Lys Pro Gly Glu Ser Val Ser Ile Ser Cys Lys Ala Ser Gly Tyr Thr
        35                  40                  45

Phe Thr Asp Ser Ala Ile His Trp Val Lys Gln Ala Pro Gly Lys Gly
    50                  55                  60

Leu Lys Tyr Met Gly Trp Ile Asn Thr Tyr Thr Gly Lys Pro Thr Tyr
65                  70                  75                  80

Ala Asp Asp Phe Lys Gly Arg Phe Val Phe Ser Leu Glu Ala Ser Ala
                85                  90                  95

Ser Thr Ala Lys Leu Gln Ile Ser Asn Leu Lys Ser Glu Asp Thr Ala
            100                 105                 110

Thr Phe Phe Cys Ala Arg Ser Val Tyr Ser Tyr Asp Gly Thr Phe Tyr
        115                 120                 125

Arg Tyr Phe Leu Asp Ala Trp Gly Gln Gly Ala Ser Val Thr Val Ser
    130                 135                 140

Ser
145

<210> SEQ ID NO 8
<211> LENGTH: 435
<212> TYPE: DNA
<213> ORGANISM: Artificial Sequence
<220> FEATURE:
<223> OTHER INFORMATION: Synthetic

<400> SEQUENCE: 8

```
atggattggg tgtggaactt gctatttctg atggcagttg cccaaacagg tgcccaagca    60
cagatccagt tggtacagtc tggacctgag ctgaagaagc tggagagtc agtgagtatc    120 tcctgcaagg cttctggtta taccttcaca gactctgcaa tactgggt gaaacaggct    180 ccaggaaagg gcttgaagta catgggctgg atcaacacct atactgggaa gccaacatat    240
gctgatgact tcaaaggacg gtttgtcttc tctttggaag cctctgccag cactgcaaag    300
ttgcagatca gcaaccctca aagtgaggac acggctacat ttttctgtgc aagatcagtt    360
tattcctatg atggtacttt ttaccgctat tttcttgatg cctggggtca aggagcttca    420
gtcactgtct cctca                                                    435
```

<210> SEQ ID NO 9
<211> LENGTH: 126
<212> TYPE: PRT
<213> ORGANISM: Artificial Sequence
<220> FEATURE:
<223> OTHER INFORMATION: Synthetic

<400> SEQUENCE: 9

```
Met Glu Thr Asp Arg Leu Leu Trp Val Leu Leu Trp Val Pro
1               5                   10                  15
Gly Ser Thr Gly Asp Thr Val Leu Thr Gln Ser Pro Ala Leu Ala Val
                20                  25                  30
Ser Pro Gly Glu Lys Val Thr Ile Ser Cys Arg Ala Ser Glu Ser Val
            35                  40                  45
Ser Lys His Ile His Trp Phe Gln Gln Lys Ser Gly Gln Gln Pro Thr
        50                  55                  60
Leu Leu Ile Tyr Leu Ala Ser Ser Leu Glu Ser Gly Val Pro Ala Arg
65                  70                  75                  80
Phe Ser Gly Ser Gly Ser Gly Thr Asp Phe Thr Leu Thr Ile Asp Pro
                85                  90                  95
Val Glu Ala Asp Asp Thr Ala Thr Tyr Tyr Cys Gln Gln Ser Trp Asn
                100                 105                 110
Asp Pro Trp Thr Phe Gly Gly Gly Thr Lys Leu Glu Leu Lys
            115                 120                 125
```

<210> SEQ ID NO 10
<211> LENGTH: 378
<212> TYPE: DNA
<213> ORGANISM: Artificial Sequence
<220> FEATURE:
<223> OTHER INFORMATION: Synthetic

<400> SEQUENCE: 10

```
atggagacag acagactcct gctatgggtg ctgctgctct gggttccagg ctccactggt    60
gacactgtac tgacccagtc tcctgctttg gctgtgtctc aggagagaa ggtaaccatc    120 tcctgtaggg ccagtgaaag tgtcagtaaa catatacact ggttccaaca gaaatcagga    180
cagcaaccca cactcctcat ctatctagca tcaagcctgg aatctgggt ccctgccagg    240 ttcagtggca gtgggtctgg gacagacttc accctcacca ttgatcctgt ggaggctgat    300
gacactgcaa cctattactg tcagcagagt tggaatgatc cgtggacgtt cggtggaggc    360
accaagctgg aattgaaa                                                 378
```

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Glu Asp Ser Val Ile Ser Leu Ser Gly Asp His Cys Ile Ile Gly Arg
1               5                   10                  15

Thr

<210> SEQ ID NO 12
<211> LENGTH: 153
<212> TYPE: PRT
<213> ORGANISM: Artificial Sequence
<220> FEATURE:
<223> OTHER INFORMATION: Synthetic

<400> SEQUENCE: 12

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Leu Ser Gly Asp His Cys Ile Ile Gly Arg Thr Leu Val Val His Glu
1               5                   10                  15

Lys

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
gactctgcaa tacac                                                    15

<210> SEQ ID NO 15

```
<211> LENGTH: 51
<212> TYPE: DNA
<213> ORGANISM: Artificial Sequence
<220> FEATURE:
<223> OTHER INFORMATION: Synthetic

<400> SEQUENCE: 15
tggatcaaca cctatactgg aagccaaca tatgctgatg acttcaaagg a              51

<210> SEQ ID NO 16
<211> LENGTH: 48
<212> TYPE: DNA
<213> ORGANISM: Artificial Sequence
<220> FEATURE:
<223> OTHER INFORMATION: Synthetic

<400> SEQUENCE: 16
tcagtttatt cctatgatgg tacttttttac cgctattttc ttgatgcc                48

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17
agggccagtg aaagtgtcag taaacatata cac                                 33

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
ctagcatcaa gcctggaatc t                                              21

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
cagcagagtt ggaatgatcc gtggacg                                        27

<210> SEQ ID NO 20
<211> LENGTH: 816
<212> TYPE: DNA
<213> ORGANISM: Artificial Sequence
<220> FEATURE:
<223> OTHER INFORMATION: Synthetic

<400> SEQUENCE: 20
atggagacag acacactcct gctatgggtg ctgctgctct gggttccagg ttccactggt    60
gaccagatcc agttggtaca gtctggacct gagctgaaga agcctggaga gtcagtgagt   120
atctcctgca aggcttctgg ttataccttc acagactctg caatacactg ggtgaaacag   180
gctccaggaa agggcttgaa gtacatgggc tggatcaaca cctatactgg gaagccaaca   240
tatgctgatg acttcaaagg acggtttgtc ttctctttgg aagcctctgc cagcactgca   300
aagttgcaga tcagcaacct caaaagtgag gacacggcta cattttttctg tgcaagatca   360
```

```
gtttattcct atgatggtac tttttaccgc tatttcttg atgcctgggg tcaaggagct      420
tcagtcactg tctcctcagg cggcggcggc agcggaggcg gcggctccgg cggcggcggc      480
tctgacactg tactgaccca gtctcctgct ttggctgtgt ctccaggaga gaaggtaacc      540
atctcctgta gggccagtga aagtgtcagt aaacatatac actggttcca acagaaatca      600
ggacagcaac ccacactcct catctatcta gcatcaagcc tggaatctgg ggtccctgcc      660
aggttcagtg gcagtgggtc tgggacagac ttcaccctca ccattgatcc tgtggaggct      720
gatgacactg caacctatta ctgtcagcag agttggaatg atccgtggac gttcggtgga      780
ggcaccaagc tggaattgaa aggcggcggc ggctct                                816

<210> SEQ ID NO 21
<211> LENGTH: 831
<212> TYPE: DNA
<213> ORGANISM: Artificial Sequence
<220> FEATURE:
<223> OTHER INFORMATION: Synthetic

<400> SEQUENCE: 21
atggagacag acacactcct gctatgggtg ctgctgctct gggttccagg ttccactggt       60
gaccagatcc agttggtaca gtctggacct gagctgaaga gcctggaga gtcagtgagt      120 atctcctgca aggcttctgg ttataccttc acagactctg caatacactg ggtgaaacag      180
gctccaggaa agggcttgaa gtacatgggc tggatcaaca cctatactgg gaagccaaca      240
tatgctgatg acttcaaagg acggtttgtc ttctctttgg aagcctctgc cagcactgca      300
aagttgcaga tcagcaacct caaaagtgag gacacggcta ttttttctg tgcaagatca      360 gtttattcct atgatggtac tttttaccgc tattttcttg atgcctgggg tcaaggagct      420
tcagtcactg tctcctcagg cggcggcggc agcggaggcg gcggctccgg cggcggcggc      480
tctggcggcg gcggcagcga cactgtactg acccagtctc ctgctttggc tgtgtctcca      540
ggagagaagg taaccatctc ctgtagggcc agtgaaagtg tcagtaaaca tatacactgg      600
ttccaacaga aatcaggaca gcaacccaca ctcctcatct atctagcatc aagcctggaa      660
tctggggtcc ctgccaggtt cagtggcagt gggtctggga cagacttcac cctcaccatt      720
gatcctgtgg aggctgatga cactgcaacc tattactgtc agcagagttg gaatgatccg      780
tggacgttcg gtggaggcac caagctggaa ttgaaaggcg gcggcggctc t               831
```

ANTI SUPEROXIDE DISMUTASE 1 (SOD1) ANTIBODIES AND USE THEREOF

CROSS REFERENCE TO RELATED APPLICATIONS

This application is a National Phase of PCT Patent Application No. PCT/IL2019/051307 having International filing date of Nov. 28, 2019 titled "ANTI SUPEROXIDE DISMUTASE 1 (SOD1) ANTIBODIES AND USE THEREOF", which claims the benefit of priority of U.S. Provisional Patent Application No. 62/772,224 titled "ANTI SUPEROXIDE DISMUTASE 1 (SOD1) ANTIBODIES AND USE THEREOF", filed Nov. 28, 2018. The contents of the above applications are all incorporated by reference as if fully set forth herein in their entirety.

FIELD OF INVENTION

The present invention is in the field of monoclonal antibodies.

BACKGROUND

Amyotrophic lateral sclerosis (ALS) is a neurodegenerative disorder that leads to motor neurons death. To date, Riluzole and Edaravone are the only FDA-approved drugs for ALS. However, these drugs only marginally slow down the disease progression, indicating a pressing need for more effective therapeutics.

Superoxide dismutase 1 (SOD1) is an ALS pathogenic protein, whose misfolding results in the formation of amyloid aggregates. The mechanism underlying SOD1 pathogenesis in ALS remains obscure, but one possible mechanism involves gain-of-interaction, in which the misfolded soluble SOD1 forms abnormal protein-protein interactions (PPIs) with various cellular proteins, including with other SOD1 molecules, thereby interfering with their function.

SUMMARY

The present invention provides monoclonal antibodies or antigen-binding portions thereof having high affinity to mutated superoxide dismutase 1 (SOD1), as well as composition comprising same and methods of use thereof.

According to a first aspect, there is provided an antibody or an antigen-binding portion thereof, the antibody comprising three heavy chain CDRs (CDR-H) and three light chain CDRs (CDR-L), wherein: CDR-H1 comprises the amino acid sequence set forth in SEQ ID NO: 1 (DSAIH), CDR-H2 comprises the amino acid sequence as set forth in SEQ ID NO: 2 (WINTYTGKPTYADDFKG), CDR-H3 comprises the amino acid sequence as set forth in SEQ ID NO: 3 (SVYSYDGTFYRYFLDA), CDR-L1 comprises the amino acid sequence as set forth in SEQ ID NO: 4 (RASESVSKHIH), CDR-L2 comprises the amino acid sequence as set forth in SEQ ID NO: 5 (LASSLES), and CDR-L3 comprises the amino acid sequence as set forth in SEQ ID NO: 6 (QQSWNDPWT).

According to another aspect, there is provided a method for treating or ameliorating amyotrophic lateral sclerosis (ALS) in a subject in need thereof, comprising administering to the subject a therapeutically effective amount of: the disclosed antibody or an antigen-binding portion thereof; the disclosed AAV vector; the disclosed pharmaceutical composition, or any combination thereof.

According to another aspect, there is provided a method of in vitro detecting misfolded SOD1 in a subject, comprising: providing a sample of bodily fluid from the subject; contacting the bodily fluid with the disclosed antibody or antigen-binding fragment thereof; and detecting the antibody or antigen-binding fragment thereof bound to misfolded SOD1, thereby detecting misfolded SOD1 in the subject.

According to another aspect, there is provided a method of in vitro detecting misfolded SOD1 in a subject, comprising: providing a sample of bodily fluid from the subject; contacting the bodily fluid with the disclosed antibody or antigen-binding fragment thereof; and detecting the antibody or antigen-binding fragment thereof bound to misfolded SOD1, thereby detecting misfolded SOD1 in the subject.

According to another aspect, there is provided a method of screening for a compound suitable for treating, preventing or inhibiting the progression of ALS, comprising contacting misfolded SOD1 with a compound, and determining the amount of antibody or an antigen-binding portion thereof bound to the misfolded SOD1 in the presence of the compound, wherein reduction of the amount of antibody or antigen-binding portion thereof bound to the misfolded SOD1 in the presence of the compound compared to the amount of antibody or antigen-binding portion thereof bound to the misfolded SOD1 in the absence of the compound, indicates the compound is suitable for treating, preventing or inhibiting the progression of ALS.

In some embodiments, the antibody or antigen-binding portion thereof comprises a heavy chain comprising the amino acid sequence of SEQ ID NO: 7.

In some embodiments, the antibody or antigen-binding portion thereof comprises a light chain comprising the amino acid sequence of SEQ ID NO: 9.

In some embodiments, the antigen binding fragment is selected from the group consisting of a Fv, Fab, F(ab')$_2$, scFv or a scFv$_2$ fragment.

In some embodiments, the antibody or antigen-binding portion thereof has specific binding affinity for misfolded SOD1.

In some embodiments, the misfolded SOD1 is a wild type SOD1 or a mutated SOD1.

In some embodiments, the wild type SOD1 is apo SOD1$^{WT}$. In some embodiments, the apo SOD1$^{WT}$ is devoid of $Cu^{2+}$, $Zn^{2+}$, or a combination thereof.

In some embodiments, the mutated SOD1 comprises one or more mutations selected from the group consisting of: glycine at position 93 to alanine (SOD1$^{G93A}$) and glycine at position 85 to arginine (SOD1$^{G85R}$).

In some embodiments, the antibody or antigen-binding portion thereof has specific binding affinity for an amino acid sequence set forth in SEQ ID NO: 11 (EDSVISLSGDHCIIGRT).

In some embodiments, the antibody or antigen-binding portion thereof is humanized.

In some embodiments, there is provided a recombinant adeno-associated virus (AAV) vector comprising one or more polynucleotide sequences encoding the disclosed antibody or an antigen-binding portion thereof.

In some embodiments, there is provided a pharmaceutical composition comprising the disclosed antibody or an antigen-binding portion thereof, the disclosed AAV vector, or a combination thereof, and a pharmaceutically acceptable carrier.

In some embodiments, the composition is for use in treating or ameliorating amyotrophic lateral sclerosis (ALS).

In some embodiments, the method comprises a step of selecting a subject having increased misfolded SOD1 levels compared to control.

In some embodiments, selecting the subject comprises: providing a sample of bodily fluid from the subject; contacting the bodily fluid with the disclosed antibody or antigen-binding fragment thereof; and determining levels of the antibody or antigen-binding fragment thereof bound to misfolded SOD1 compared to control.

In some embodiments, the antibody or antigen-binding portion thereof binds to a misfolded SOD1 of the subject.

In some embodiments, the antibody or antigen-binding portion thereof binds to an amino acid sequence set forth in SEQ ID NO: 11 of the subject.

In some embodiments, the antibody or antigen-binding portion thereof blocks the misfolded SOD1, blocks the amino acid sequence set forth in SEQ ID NO: 11, or blocks both.

In some embodiments, the antibody or antigen-binding portion thereof prevents or reduces the rate of oligomerization or aggregation of the misfolded SOD1 in the subject.

In some embodiments, the rate of oligomerization or aggregation of the misfolded SOD1 is prevented or reduced is the serum or a tissue of the subject.

In some embodiments, the tissue is selected from the group consisting of muscle tissue and neural tissue.

In some embodiments, the subject is afflicted by ALS.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
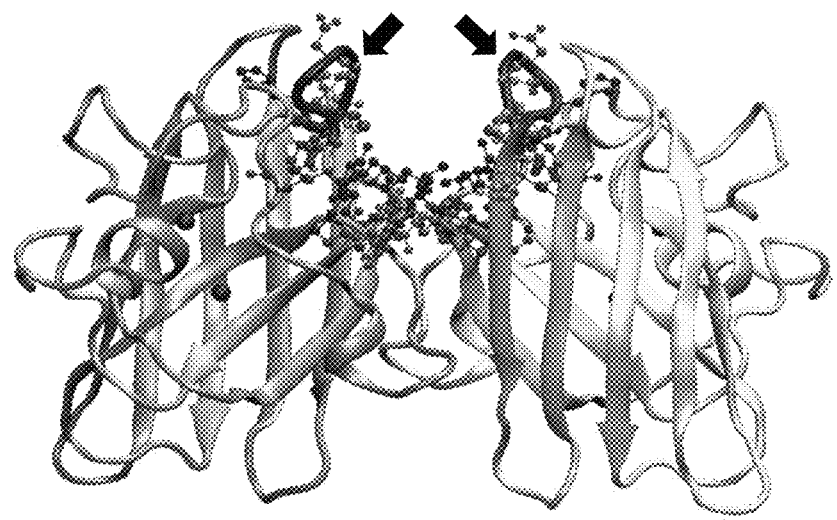
FIGS. 1A-1B are an image and a graph showing (1A) the surface pocket shaped by the two β6/β7 loops (arrows) in the intact SOD1$^{WT}$ dimer, and (1B) the results of enzyme linked immunosorbent assay (ELISA) of supernatants of several hybridoma clones expressing anti-β6/β7-loop monoclonal antibody (mAb) using SOD1 variants as coating antigens. NC—negative control. WT—wild type; apo—WT in the absence of metals ($Cu^{2+}$ and $Zn^{2+}$); holo—WT in the presence of metals ($Cu^{2+}$ and $Zn^{2+}$); G93A—Glycine at position 93 was substituted to Alanine; G85R—Glycine at position 85 was substituted to Arginine; antigen peptide—peptide used to produce the disclosed mAb.
Figure 1B:
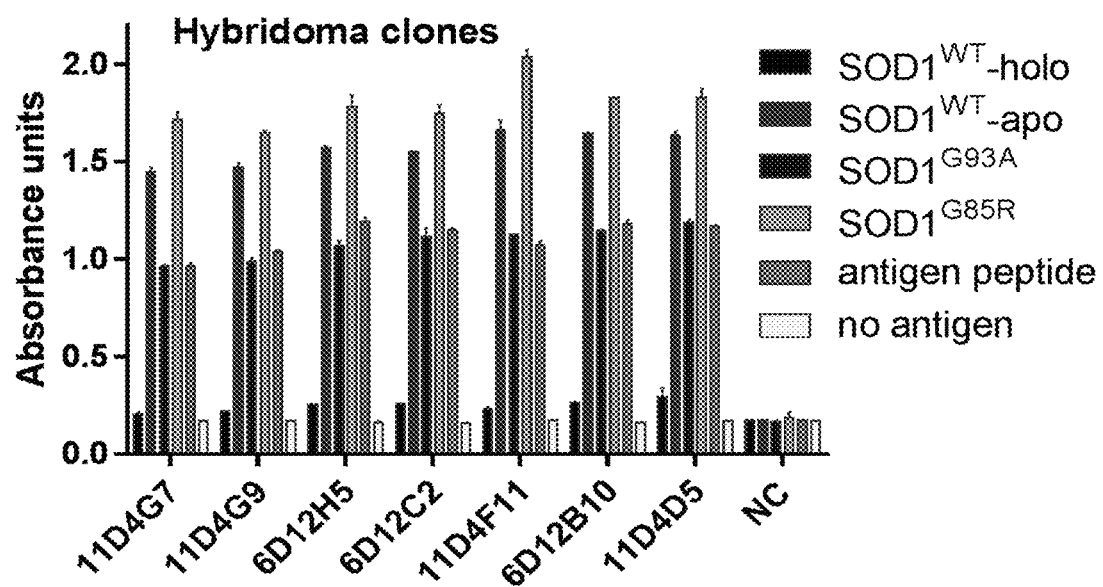

The present invention, in some embodiments thereof, provides antibodies or antibody fragments thereof having strong binding to superoxide dismutase 1 (SOD1), specifically to a putative aggregation-initiating 06437 loop epitope of a misfolded SOD1. The present invention, in some embodiments thereof, is further directed to methods of using the disclosed antibody, such as in drug screening, diagnosis, or immunotherapy of ALS, as well as kits comprising the antibodies of the invention or fragments thereof.

By a first aspect, there is provided an antibody or an antigen-binding portion thereof, comprising three heavy chain CDRs (CDR-H) and three light chain CDRs (CDR-L), wherein: CDR-H1 comprises the amino acid sequence set forth in SEQ ID NO: 1 (DSAIH), CDR-H2 comprises the amino acid sequence as set forth in SEQ ID NO: 2 (WINTYTGKPTYADDFKG), CDR-H3 comprises the amino acid sequence as set forth in SEQ ID NO: 3 (SVYSYDGTFYRYFLDA), CDR-L1 comprises the amino acid sequence as set forth in SEQ ID NO: 4 (RASESVSKHIH), CDR-L2 comprises the amino acid sequence as set forth in SEQ ID NO: 5 (LASSLES), and CDR-L3 comprises the amino acid sequence as set forth in SEQ ID NO: 6 (QQSWNDPWT).

In some embodiments, the antibody or antigen-binding fragment thereof comprises a heavy chain comprising the amino acid sequence MDWVWNLLFLMAVAQT-GAQAQIQLVQSGPELKKPGESVSISCKASGYTFTD-SAIH WVKQAPGKGLKYMGWINTYTGKPTY-ADDFKGRFVFSLEASASTAKLQISNLKSED TATFFCARSVYSYDGTFYRYFLDAWGQGASVTVSS (SEQ ID NO: 7). In some embodiments, the variable region of the heavy chain comprises and/or consists of SEQ ID NO: 7. In some embodiments, the variable region of a heavy chain of an antibody or antigen-binding fragment thereof is encoded by a polynucleotide sequence as set forth in SEQ ID NO: 8

```
(ATGGATTGGGTGTGGAACTTGCTATTTCTGATGGC

AGTTGCCCAAACAGGTGCCCAAGCACAGATCCAGT

TGGTACAGTCTGGACCTGAGCTGAAGAAGCCTGGA

GAGTCAGTGAGTATCTCCTGCAAGGCTTCTGGTTA

TACCTTCACAGACTCTGCAATACACTGGGTGAAAC

AGGCTCCAGGAAAGGGCTTGAAGTACATGGGCTGG

ATCAACACCTATACTGGGAAGCCAACATATGCTGA

TGACTTCAAAGGACGGTTTGTCTTCTCTTTGGAAG

CCTCTGCCAGCACTGCAAAGTTGCAGATCAGCAAC

CTCAAAAGTGAGGACACGGCTACATTTTTCTGTGC

AAGATCAGTTTATTCCTATGATGGTACTTTTTACC

GCTATTTTCTTGATGCCTGGGGTCAAGGAGCTTCA

GTCACTGTCTCCTCA).
```

In some embodiments, the antibody or antigen-binding fragment thereof comprises a light chain comprising the amino acid sequence METDRLLLWVLLLWVPG-STGDTVLTQSPALAVSPGEKVTISCRASESVSKH-IHWFQ QKSGQQPTLLIY-LASSLESGVPARFSGSGSGTDFTLTIDPVEADDTATYY CQQSWND PWTFGGGTKLELK (SEQ ID NO: 9). In some embodiments, the variable region of the heavy chain comprises and/or consists of SEQ ID NO: 9. In some embodiments, the variable region of a heavy chain of an antibody or antigen-binding fragment thereof is encoded by a polynucleotide sequence as set forth in SEQ ID NO: 10

(ATGGAGACAGACAGACTCCTGCTATGGGTGCTGCT

GCTCTGGGTTCCAGGCTCCACTGGTGACACTGTAC

TGACCCAGTCTCCTGCTTTGGCTGTGTCTCCAGGA

GAGAAGGTAACCATCTCCTGTAGGGCCAGTGAAAG

TGTCAGTAAACATATACACTGGTTCCAACAGAAAT

CAGGACAGCAACCCACACTCCTCATCTATCTAGCA

TCAAGCCTGGAATCTGGGGTCCCTGCCAGGTTCAG

TGGCAGTGGGTCTGGGACAGACTTCACCCTCACCA

TTGATCCTGTGGAGGCTGATGACACTGCAACCTAT

TACTGTCAGCAGAGTTGGAATGATCCGTGGACGTT

CGGTGGAGGCACCAAGCTGGAATTGAAA).

The term "antibody" (also referred to as an "immunoglobulin") is used in the broadest sense and specifically encompasses monoclonal antibodies and antibody fragments so long as they exhibit the desired biological activity. In certain embodiments, the use of a chimeric antibody or a humanized antibody is also encompassed by the invention. In some embodiments, the antibody is a humanized antibody comprising the CDRs of the invention.

Generally, an antibody refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)-Fc fusions and scFv-scFv-Fc fusions.

In some embodiments, the antibody of the invention is a single chain variable fragment (scFv).

In some embodiments, the scFv comprises an amino acid linker positioned between the heavy chain and the light of the scFv. In some embodiments, the amino acid linker comprises at least 7, at least 10, at least 13, at least 15, at least 17, at least 20, or at least 25 amino acids, or any value and range therebetween. Each possibility represents a separate embodiment of the invention. In some embodiments, the amino acid linker comprises 7 to 15, 10 to 22, 11 to 19, 12 to 25, 14 to 22, 13 to 18, 13 to 23, or 17 to 22 amino acid. Each possibility represents a separate embodiment of the invention.

In some embodiments, the linker comprises any number of amino acids as long as it serves only as a spacer between the heavy chain and the light chain of the scFv and has no functional significance with respect to antigen or epitope binding. In some embodiments, the linker comprises any number of amino acids as long as it does not impose steric interference over the heavy chain, the light chain, or both, of the scFv which in turn negatively affects antigen or epitope binding, for example, reduces binging affinity.

In some embodiments, the amino acid linker comprises glycine residues, serine residues, or any combination thereof. In some embodiments, the amino acid linker comprises 5 consecutive amino acids comprising 4 glycine residues and 1 serine residue. In some embodiments, the scFv comprises repeats of the 5 consecutive amino acids. In some embodiments, the scFv comprises al to 6, 2 to 8, or 3 to 7 repeats of the 5 consecutive amino acids.

In some embodiments, the scFv is encoded by a DNA polynucleotide sequence comprising or consisting of the polynucleotide sequence:

(SEQ ID NO: 20)
ATGGAGACAGACACACTCCTGCTATGGGTGCTGCT

GCTCTGGGTTCCAGGTTCCACTGGTGACCAGATCC

AGTTGGTACAGTCTGGACCTGAGCTGAAGAAGCCT

GGAGAGTCAGTGAGTATCTCCTGCAAGGCTTCTGG

TTATACCTTCACAGACTCTGCAATACACTGGGTGA

AACAGGCTCCAGGAAAGGGCTTGAAGTACATGGGC

TGGATCAACACCTATACTGGGAAGCCAACATATGC

TGATGACTTCAAAGGACGGTTTGTCTTCTCTTTGG

AAGCCTCTGCCAGCACTGCAAAGTTGCAGATCAGC

AACCTCAAAAGTGAGGACACGGCTACATTTTTCTG

TGCAAGATCAGTTTATTCCTATGATGGTACTTTTT

ACCGCTATTTTCTTGATGCCTGGGGTCAAGGAGCT

TCAGTCACTGTCTCCTCAGGCGGCGGCGGCAGCGG

AGGCGGCGGCTCCGGCGGCGGCGGCTCTGACACTG

TACTGACCCAGTCTCCTGCTTTGGCTGTGTCTCCA

GGAGAGAAGGTAACCATCTCCTGTAGGGCCAGTGA

AAGTGTCAGTAAACATATACACTGGTTCCAACAGA

AATCAGGACAGCAACCCACACTCCTCATCTATCTA

-continued

```
GCATCAAGCCTGGAATCTGGGGTCCCTGCCAGGTT

CAGTGGCAGTGGGTCTGGGACAGACTTCACCCTCA

CCATTGATCCTGTGGAGGCTGATGACACTGCAACC

TATTACTGTCAGCAGAGTTGGAATGATCCGTGGAC

GTTCGGTGGAGGCACCAAGCTGGAATTGAAAGGCG

GCGGCGGCTCT.
```

In some embodiments, the scFv is encoded by a DNA polynucleotide sequence comprising or consisting of the polynucleotide sequence:

```
                                        (SEQ ID NO: 21)
ATGGAGACAGACACACTCCTGCTATGGGTGCTGCT

GCTCTGGGTTCCAGGTTCCACTGGTGACCAGATCC

AGTTGGTACAGTCTGGACCTGAGCTGAAGAAGCCT

GGAGAGTCAGTGAGTATCTCCTGCAAGGCTTCTGG

TTATACCTTCACAGACTCTGCAATACACTGGGTGA

AACAGGCTCCAGGAAAGGGCTTGAAGTACATGGGC

TGGATCAACACCTATACTGGGAAGCCAACATATGC

TGATGACTTCAAAGGACGGTTTGTCTTCTCTTTGG

AAGCCTCTGCCAGCACTGCAAAGTTGCAGATCAGC

AACCTCAAAAGTGAGGACACGGCTACATTTTTCTG

TGCAAGATCAGTTTATTCCTATGATGGTACTTTTT

ACCGCTATTTCTTGATGCCTGGGGTCAAGGAGCT

TCAGTCACTGTCTCCTCAGGCGGCGGCGGCAGCGG

AGGCGGCGGCTCCGGCGGCGGCGGCTCTGGCGGCG

GCGGCAGCGACACTGTACTGACCCAGTCTCCTGCT

TTGGCTGTGTCTCCAGGAGAGAAGGTAACCATCTC

CTGTAGGGCCAGTGAAAGTGTCAGTAAACATATAC

ACTGGTTCCAACAGAAATCAGGACAGCAACCCACA

CTCCTCATCTATCTAGCATCAAGCCTGGAATCTGG

GGTCCCTGCCAGGTTCAGTGGCAGTGGGTCTGGGA

CAGACTTCACCCTCACCATTGATCCTGTGGAGGCT

GATGACACTGCAACCTATTACTGTCAGCAGAGTTG

GAATGATCCGTGGACGTTCGGTGGAGGCACCAAGC

TGGAATTGAAAGGCGGCGGCGGCTCT.
```

Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody comprises IgG2 or IgG4. In some embodiments, the antibody comprises IgG2. In some embodiments, the antibody comprises IgG4.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (imgt.-cines.fr/) (IMGT®/V-Quest) to identify variable region segments, including CDRs. See, e.g., Brochet, X. et al, Nucl. Acids Res. J6: W503-508 (2008).

Chothia et al. also defined a numbering system for variable domain sequences that is applicable to any antibody. One of ordinary skill in the art can unambiguously assign this system of "Chothia numbering" to any variable domain sequence, without reliance on any experimental data beyond the sequence itself. As used herein, "Chothia numbering" refers to the numbering system set forth by Chothia et al., Journal of Molecular Biology, "Canonical Structures for the Hypervariable regions of immunoglobulins" (1987) and Chothia et al., Nature, "Conformations of Immunoglobulin Hypervariable Regions" (1989).

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed antibodies to be used in accordance with the methods provided herein may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multi-specific antibodies formed from antibody fragments (e.g., including but not limited to, Db-Fc, taDb-Fc, taDb-CH3, (scFv)4-Fc, di-scFv, bi-scFv, or tandem (di, tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are Natl. Acad. Sci. USA, 90:6444-6448 (1993).

The term "multi-specific antibody" is used in the broadest sense and specifically covers an antibody that has poly-epitopic specificity. Such multi-specific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include: antibodies, fragments of antibodies, Fab and F(ab') 2, single-domain antigen-binding recombinant fragments and natural nanobodies. In some embodiments, the antigen binding fragment is selected from the group consisting of a Fv, Fab, F(ab')2, scFv or a scFV2 fragment.

In some embodiments, the present invention provides nucleic acid sequences encoding the antibodies or antigen binding portions of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

In some embodiments, the antibody or antigen binding fragment thereof is an anti-SOD1 antibody. In some embodiments, the antibody or antigen binding fragment thereof is an anti-misfolded SOD1 antibody. In some embodiments, the target antigen of the antibody is $\beta 6/\beta 7$ loop of SOD1. In some embodiments, the target antigen of the antibody is $\beta 6/\beta 7$ loop of a misfolded SOD1. In some embodiments, the target antigen of the antibody is a polypeptide sequence as set forth in SEQ ID NO: 11 (EDSVISLSGDHCIIGRT). In some embodiments, the target antigen of the antibody is mutated SOD1. In some embodiments, the mutated SOD1 is selected from the group consisting of: $SOD1^{G93A}$, and $SOD1^{G85R}$. In some embodiments, the target antigen of the antibody is a wild type SOD1. In some embodiments, the antibody or antigen binding fragment thereof binds to a wild type SOD1 in the absence of ions (apo $SOD1^{WT}$). In some embodiments, the antibody or antigen binding fragment thereof binds to a wild type SOD1 in the absence of Cu' ions. In some embodiments, the antibody or antigen binding fragment thereof binds to a wild type SOD1 in the absence of $Zn^{2+}$ ions. In some embodiments, the antibody or antigen binding fragment thereof binds to a wild type SOD1 in the absence of $Cu^{2+}$ and $Zn^{2+}$. In some embodiments, the antibody or antigen binding fragment thereof has specific affinity to an apo $SOD1^{WT}$. In some embodiments, the antibody or antigen binding fragment thereof has low or no affinity to a wild type SOD1 in the presence of an ion selected from the group consisting of $Cu^{2+}$ and $Zn^{2+}$ (holo $SOD1^{WT}$).

An "anti-misfolded SOD1 antibody", "an antibody which recognizes misfolded SOD1", or "an antibody against misfolded SOD1" is an antibody that binds misfolded SOD1, with sufficient affinity and specificity. In some embodiments, the antibody has increased binding to any one of the SOD1 proteins selected from the group consisting of: misfolded SOD1 and mutated SOD1 (e.g., $SOD1^{G93A}$, and $SOD1^{G85R}$). In some embodiments, the antibody has increased binding to misfolded SOD1 as compared to natively folded SOD1. In some embodiments, the antibody has increased binding to mutated SOD1 as compared to natively folded SOD1. In some embodiments, the antibody has increased binding to $SOD1^{G93A}$ as compared to natively folded SOD1. In some embodiments, the antibody has increased binding to misfolded SOD1 as compared to natively folded SOD1$^{G85R}$. In some embodiments, the antibody has increased binding to apo SOD1$^{WT}$ as compared to natively folded SOD1. In some embodiments, the antibody or antigen-binding fragment thereof has specific binding affinity for misfolded or mutated SOD1.

As used herein, the term "misfolded SOD1" encompasses any SOD1 protein folded in a manner in which the β6/β7 loop region is exposed on the protein surface and capable of protein-protein interaction. In some embodiments, the β6/β7 loop region comprises an amino acid sequence set forth in SEQ ID NO: 11. In one embodiment, the misfolded SOD1 is at least partially misfolded compared to the natively folded SOD1. In one embodiment, misfolded SOD1 is a mutated SOD1.

In some embodiments, the misfolded or partially misfolded SOD1 has less than 100% structural homology to the natively folded SOD1. In some embodiments, the misfolded or partially misfolded SOD1 has structural homology to the natively folded SOD1 of 99.99% at most, 99.9% at most, 99% at most, 95% at most, 90% structural homology at most, or any range or value therebetween. In some embodiments, the misfolded or partially misfolded SOD1 has structural homology to the natively folded SOD1 of 80-90%, 95-99.9%, or 99-99.99%. Each possibility represents a separate embodiment of the invention.

As used herein, the terms "increased binding affinity" and "greater binding affinity" are interchangeable. In some embodiments, antibody or antigen-binding portion thereof of the present invention has a greater binding affinity to a misfolded or mutated SOD1 compared to the natively folded SOD1. In one embodiment, greater affinity as used herein is by 5-10%. In one embodiment, greater affinity as used herein is by 8-30%. In one embodiment, greater affinity as used herein is by 25-50%. In one embodiment, greater affinity as used herein is by 40-75%. In one embodiment, greater affinity as used herein is by 65-100%. In one embodiment, greater affinity as used herein is by 90-150%. In one embodiment, greater affinity as used herein is by 125-250%. In one embodiment, greater affinity as used herein is by 200-500%. In one embodiment, greater affinity as used herein is by 450-1,000%. In one embodiment, greater affinity as used herein is by 1.5-fold. In one embodiment, greater affinity as used herein is by 2-fold. In one embodiment, greater affinity as used herein is by 5-fold. In one embodiment, greater affinity as used herein is by 10-fold. In one embodiment, greater affinity as used herein is by 50-fold. In one embodiment, greater affinity as used herein is by 100-fold. In one embodiment, greater affinity as used herein is by 500-fold. In one embodiment, greater affinity as used herein is by 1,000-fold.

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies.

In some embodiments, the SOD1 is mammalian SOD1. In some embodiments the SOD1 is human SOD1. In some embodiments, the human SOD1 comprises or consists of the amino acid sequence: ATKAVCVLKGDGPVQGIINFEQKESNGPVKVWGSIKGLTEGLHGFHVHEFGDNTAG CTSAGPHFNPLSRKHGGPKDEERHVGDLGNVTADKDGVADVSIEDSVISLSGDHCII GRTLVVHEKADDLGKGGNEESTKTGNAGSRLACGVIGIAQ (SEQ ID NO: 12). In some embodiments, a mutated SOD1 comprises a substitution of Glycine for Alanine at position 93 (G93A). In some embodiments, a mutated SOD1 comprises a substitution of Glycine for Arginine at position 85 (G85R).

In some embodiments, the binding of the antibody of the invention or antigen-binding region thereof to misfolded SOD1 prevents SOD1 oligomerization. In some embodiments, the binding of the antibody of the invention or antigen-binding region thereof to misfolded SOD1 inhibits SOD1 oligomerization. In some embodiments, the binding of the antibody of the invention or antigen-binding region thereof to misfolded SOD1 reduces rates of SOD1 oligomerization. In some embodiments, the binding of the antibody of the invention or antigen-binding region thereof to misfolded SOD1 reduces SOD1 aggregation. In some embodiments, the binding of the antibody of the invention or antigen-binding region thereof to misfolded SOD1 inhibits initiation of the misfolding signal of structurally intact SOD1 molecules. In some embodiments, the binding of the antibody of the invention or antigen-binding region thereof to misfolded SOD1 inhibits propagation of the misfolding signal of structurally intact SOD1 molecules. In some embodiments, the binding of the antibody of the invention or antigen-binding region thereof to misfolded SOD1 inhibits prion-like propagation of the misfolding signal of structurally intact SOD1 molecules. In some embodiments, the binding of the antibody of the invention or antigen-binding region thereof to misfolded SOD1 stabilizes misfolded SOD1. In some embodiments, the binding of the antibody of the invention or antigen-binding region thereof to misfolded SOD1 blocks the site of SOD1 oligomerization. In some embodiments, the binding of the antibody of the invention or antigen-binding region thereof to misfolded SOD1 blocks the site responsible for the initiation of SOD1 misfolding signal. In some embodiments, the binding of the antibody of the invention or antigen-binding region thereof to misfolded SOD1 blocks the site responsible for the propagation of SOD1 misfolding signal.

In some embodiments, the binding of the antibody of the invention or antigen-binding region thereof to misfolded SOD1 prevents protein oligomerization. In some embodiments, the binding of the antibody of the invention or antigen-binding region thereof to misfolded SOD1 inhibits protein oligomerization. In some embodiments, the binding of the antibody of the invention or antigen-binding region thereof to misfolded SOD1 reduces rates of protein oligomerization. In some embodiments, the binding of the antibody of the invention or antigen-binding region thereof to misfolded SOD1 reduces protein aggregation. In some embodiments, the binding of the antibody of the invention or antigen-binding region thereof to misfolded SOD1 inhibits initiation of the misfolding of structurally intact proteins. In some embodiments, the binding of the antibody of the invention or antigen-binding region thereof to misfolded SOD1 inhibits propagation of the misfolding structurally intact proteins. In some embodiments, the binding of the antibody of the invention or antigen-binding region thereof to misfolded SOD1 inhibits prion-like propagation of the misfolding signal of structurally intact proteins. In some embodiments, the binding of the antibody of the invention or antigen-binding region thereof to misfolded SOD1 blocks the site responsible for the initiation of protein misfolding signal. In some embodiments, the binding of the antibody of the invention or antigen-binding region thereof to misfolded SOD1 blocks the site responsible for the propagation of protein misfolding signal.

In some embodiments, the protein is not SOD1.

In some embodiments, the antibody is a single domain antibody. In some embodiments, the antibody lacks a Fc domain. In some embodiments, the antibody is a single-domain antibody. In some embodiments, the antibody is a camelid, shark or nanoantibody. In some embodiments, the antibody or fragment is fused to another protein or fragment of a protein. In some embodiments, the second protein or fragment increases half-life, particularly in serum. In some embodiments, the half-life extending protein is human serum albumin. In some embodiments, the antibody is modified by a chemical that produces a modification that enhances half-life. In some embodiments, the modification is PEGylation and the chemical is polyethylene glycol. A skilled artisan will appreciate that any half-life extending protein or chemical agent, or modification known in the art may be used. In some embodiments, the binding of the antibody of the invention or antigen-binding region thereof to misfolded SOD1 prevents SOD1 oligomerization. In some embodiments, the binding of the antibody of the invention or antigen-binding region thereof to misfolded SOD1 inhibits SOD1 oligomerization. In some embodiments, the binding of the antibody of the invention or antigen-binding region thereof to misfolded SOD1 reduces rates of SOD1 oligomerization. In some embodiments, the binding of the antibody of the invention or antigen-binding region thereof to misfolded SOD1 reduces SOD1 aggregation. In some embodiments, the binding of the antibody of the invention or antigen-binding region thereof to misfolded SOD1 inhibits initiation of the misfolding signal of structurally intact SOD1 molecules. In some embodiments, the binding of the antibody of the invention or antigen-binding region thereof to misfolded SOD1 inhibits propagation of the misfolding signal of structurally intact SOD1 molecules. In some embodiments, the binding of the antibody of the invention or antigen-binding region thereof to misfolded SOD1 inhibits prion-like propagation of the misfolding signal of structurally intact SOD1 molecules. In some embodiments, the binding of the antibody of the invention or antigen-binding region thereof to misfolded SOD1 stabilizes misfolded SOD1. In some embodiments, the binding of the antibody of the invention or antigen-binding region thereof to misfolded SOD1 blocks the site of SOD1 oligomerization. In some embodiments, the binding of the antibody of the invention or antigen-binding region thereof to misfolded SOD1 blocks the site responsible for the initiation of SOD1 misfolding signal. In some embodiments, the binding of the antibody of the invention or antigen-binding region thereof to misfolded SOD1 blocks the site responsible for the propagation of SOD1 misfolding signal.

In some embodiments, the antibody is a diagnostic antibody. In some embodiments, the antibody is a therapeutic antibody. In some embodiments, the antibody is an anti-ALS antibody.

In some embodiments, the therapeutic antibody is a neutralizing antibody. In some embodiments, the therapeutic antibody is a neutralizing antibody. In some embodiments, the therapeutic antibody is a sweeping antibody. In some embodiments, the therapeutic antibody induces antibody-dependent cell cytotoxicity (ADCC). In some embodiments, the therapeutic antibody induces complement-dependent cytotoxicity (CDC).

In one embodiment, a sweeping antibody as used herein, does not induce ADCC, CDC, or both.

In some embodiments, the antibody is for use in treating and/or preventing ALS in a subject in need thereof. In some embodiments, the antibody is for use in improving immunotherapy in a subject in need thereof. In some embodiments, the immunotherapy is misfolded SOD-based immunotherapy.

As used herein, the term "immunotherapy" encompasses a method of treating or ameliorating at least one symptom of ALS using the herein disclosed antibody.

By another aspect, there is provided a recombinant vector comprising one or more polynucleotide sequences encoding the antibody or an antigen-binding portion thereof of the invention.

In some embodiments, the vector comprises a polynucleotide set forth in SEQ ID NO: 14 (GACTCTGCAATA-CAC).

In some embodiments, the vector comprises a polynucleotide set forth in SEQ ID NO: 15

(TGGATCAACACCTATACTGGGAAGCCAACATATGC

TGATGACTTCAAAGGA).

In some embodiments, the vector comprises a polynucleotide set forth in SEQ ID NO: 16 (TCAGTTTATTCCTAT-GATGGTACTTTTTACCGCTATTTTCTTGATGCC).

In some embodiments, the vector comprises a polynucleotide set forth in SEQ ID NO: 17 (AGGGCCAGT-GAAAGTGTCAGTAAACATATACAC).

In some embodiments, the vector comprises a polynucleotide set forth in SEQ ID NO: 18 (CTAGCATCAAGCCTG-GAATCT).

In some embodiments, the vector comprises a polynucleotide set forth in SEQ ID NO: 19 (CAGCAGAGTTGGAAT-GATCCGTGGACG).

In some embodiments, the vector comprises a polynucleotide set forth in SEQ ID NO: 8.

In some embodiments, the vector comprises a polynucleotide set forth in SEQ ID NO: 10.

In some embodiments, the vector encodes a scFv antibody fragment comprising the $V_H$ and $V_L$ domains of an antibody, present in a single polypeptide chain. In some embodiments, the vector-encoded FV polypeptide further comprises a polypeptide linker between the $V_H$ and $V_L$ domains that enables the scFv to form the desired structure for antigen binding.

In one embodiment, the expression vector may further include additional polynucleotide sequences that allow, for example, the translation of several proteins from a single mRNA such as an internal ribosome entry site (IRES). In some embodiments, the vector is capable of crossing the blood-brain barrier (BBB).

Molecular vectors capable of expressing the disclosed herein polynucleotides and/or encoding the antibody of the invention are common and would be apparent to one of ordinary skill in the art.

Non-limiting examples of vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, the expression vectors may contain regulatory elements from eukaryotic viruses such as retroviruses. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as targeting specificity, are used for in vivo expression of the antibody of the present invention or antigen-binding portion thereof. In one embodiment, viral vectors produced are able to spread laterally, the result of which is that a large area becomes rapidly infected, most of which was not initially infected by the original viral particles. In another embodiment, viral vectors produced are unable to spread laterally. In one embodiment, this characteristic can be useful if the desired purpose is to introduce a specified gene into only a localized number of targeted cells.

According to some embodiments, there is provided a recombinant adeno-associated vector (AAV) comprising one or more polynucleotide sequences encoding the antibody or an antigen-binding portion thereof of the invention.

In some embodiments, the AAV encodes a scFv antibody fragment comprising the $V_H$ and $V_L$ domains of an antibody, present in a single polypeptide chain. In some embodiments, the AAV-encoded Fv polypeptide further comprises a polypeptide linker between the $V_H$ and $V_L$ domains that enables the scFv to form the desired structure for antigen binding.

In some embodiments, the AAV crosses the BBB.

In some embodiments, the AAV further comprises at least one restriction enzyme recognition sequence, a tag, or a combination thereof.

In some embodiments, the tag is a c-Myc tag. In some embodiments, the tag is for detection, isolation, purification, or any combination thereof, of a protein encoded from a polynucleotide cloned into the AAV.

By another aspect, there is provided a pharmaceutical composition comprising the antibody or antigen-binding portion thereof of the invention and a pharmaceutically acceptable carrier, excipient or adjuvant.

As used herein, the term "carrier", "excipient", or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose; starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

According to another embodiment, there is provided a method for treating or ameliorating ALS in a subject in need thereof, comprising administering to the subject a therapeutically effective amount of an antibody of the invention or an antigen-binding portion thereof, an AAV vector encoding the antibody of the invention, or a pharmaceutical composition comprising thereof.

According to another embodiment, there is provided a method for preventing or inhibiting the progression of ALS in a subject in need thereof, comprising administering to the subject a therapeutically effective amount of an antibody of the invention or an antigen-binding portion thereof, an AAV vector encoding the antibody of the invention, or a pharmaceutical composition comprising thereof.

In some embodiments, the subject is afflicted by ALS. In some embodiments, ALS is sporadic ALS. In some embodiments, ALS is familial ALS. In some embodiments, the subject bears a mutated SOD1 gene. In some embodiments, the subject is diagnosed at early stage of ALS.

In some embodiments, the subject comprises elevated levels of serum misfolded SOD1. In some embodiments, the subject comprises elevated levels of serum misfolded mutated SOD1. In some embodiments, the subject comprises elevated levels of tissue misfolded SOD1. In some embodiments, the subject comprises elevated levels of tissue misfolded mutated SOD1. In some embodiments, the levels are elevated as compared to a healthy control. In some embodiments, the levels are elevated as compared to a predetermined healthy level.

As used herein, elevated is by at least 5%, at least 10%, at least 25%, at least 40%, at least 55%, at least 70%, at least 90%, at least 100%, at least 200%, at least 350%, at least 500%, at least 1,000% compared to control, or any value or range therebetween. In some embodiments, elevated is by 1-10%, 5-25%, 20-50%, 40-80%, 75-150%, 100-250%, 200-500%, 450-800%, or 750-1,000% compared to control. Each possibility represents a separate embodiment of the invention.

In some embodiments, the method further comprises determining misfolded levels in the serum of the subject. In some embodiments, the method further comprises determining misfolded levels in a tissue of the subject. In some embodiments, the method further comprises determining suitability of the subject for treatment and/or immunotherapy by determining misfolded SOD1 levels in the serum of the subject, wherein elevated levels compared to indicate suitability for treatment.

In some embodiments, the term "control" as used herein, is a sample derived from the subject before he was diagnosed with ALS. In some embodiments, the control is a sample derived from a healthy subject. In some embodiments, the control is a sample derived from a non-ALS subject. In some embodiments, the control is a sample derived from a non-fALS subject.

As used herein, the term "bodily fluid" encompasses any fluid obtained from a living organism. In one embodiment, bodily fluid comprises serum. In one embodiment, bodily fluid comprises plasma. Other non-limiting examples for bodily fluids include, but are not limited to, vitreous fluid, lymph fluid, synovial fluid, follicular fluid, seminal fluid, amniotic fluid, milk, whole blood, urine, cerebrospinal fluid, saliva, sputum, tears, perspiration, mucus, and tissue culture media, including tissue extracts such as homogenized tissue, and cellular extracts. Methods for obtaining a biological sample is well within the capabilities of those skilled in the art.

In some embodiments, the immunotherapy is misfolded SOD1-based immunotherapy. In some embodiments, the misfolded SOD1-based immunotherapy comprises immunotherapy targeting the amino acid sequence set forth in SEQ ID NO: 11 of the misfolded SOD1. In some embodiments, the misfolded SOD1-based immunotherapy comprises administering an anti-misfolded SOD1 antibody or antigen binding portion thereof.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the terms "administering", "administration", and like terms refer to any method which, in sound medical practice, delivers a composition containing an active agent to a subject in such a manner as to provide a therapeutic effect. Suitable routes of administration can include intrathecal, oral, parenteral, subcutaneous, intravenous, intramuscular, or intraperitoneal.

By another aspect, there is provided use of a misfolded SOD1 immunotherapy, or immunotherapeutic agent, to treat ALS.

According to another embodiment, there is provided a method of in vitro detecting misfolded SOD1 in a subject in need thereof, comprising: (a) providing a sample of bodily fluid from the subject; (b) contacting the bodily fluid with an antibody or antigen binding fragment thereof of the invention; and (c) detecting the antibody or antigen binding fragment thereof bound to misfolded SOD1; thereby detecting misfolded SOD1 in the subject.

In some embodiments, a subject detected with misfolded SOD1 is further treated with the antibody of the invention or an antigen-binding portion thereof. In some embodiments, a subject detected with misfolded SOD1 is further treated with the AAV vector as disclosed hereinabove. In some embodiments, a subject detected with misfolded SOD1 is further treated with pharmaceutical composition comprising the antibody of the invention or an antigen-binding portion thereof, the AAV vector, or any combination thereof. In some embodiments, a subject detected with misfolded SOD1 is further treated with a small molecule.

In some embodiments, the small molecule has specific binding affinity to a misfolded SOD1. In some embodiments, the small molecule has specific binding affinity to an amino acid sequence set forth in SEQ ID NO: 11. In some embodiments, the small molecule has specific binding affinity to a misfolded SOD having an exposed amino acid sequence set forth in SEQ ID NO: 11. The term "exposed" refers to a given amino acid sequence that is in contact with the surrounding environment and is not folded, for example within the core of a protein, such as in a hydrophobic patch, and therefore is not isolated from the environment. In some embodiments, binding of a misfolded SOD to a small molecule reduces its immunogenicity to the antibody of the invention. In some embodiments, the antibody of the invention had reduced binding affinity to a misfolded SOD1 bound to a small molecule compared to a misfolded SOD1 that is not bound to a small molecule. In some embodiments, the small molecule stabilizes misfolded SOD1 in a monomeric state. In some embodiments, the small molecule inhibits or reduces the rate of misfolded SOD1 oligomerization or aggregation. In some embodiments, the small molecule inhibits or reduces initiation of misfolded SOD1 oligomerization or aggregation. In some embodiments, the small molecule is a therapeutic drug.

In some embodiments, detecting the antibody bound to misfolded SOD1 comprises determining the amount of bound misfolded SOD1. In some embodiments, detecting the amount of bound misfolded SOD1 is determining the amount of misfolded SOD1 in the bodily fluid. In some embodiments, the method is for determining suitability of the subject to be treated with the pharmaceutical composition of the invention. In some embodiments, a level of misfolded SOD1 above a predetermined threshold indicates the subject is suitable for treatment with the composition of the invention. In some embodiments, the method is for determining suitability of the subject for immunotherapy. In some embodiments, a level of misfolded SOD1 above a predetermined threshold indicates the subject is suitable for immunotherapy.

Methods for detecting the presence of a misfolded protein, e.g., SOD1, are common and would be apparent to one of ordinary skill in the art. Non-limiting example includes, but is not limited to binding assay with an antibody having specific binding affinity to the misfolded protein form, wherein the antibody has not or very low binding affinity to the folded form if the protein, such as exemplified herein below.

Conventional in vivo and or vitro models for studying ALS are known and would be apparent to one of ordinary skill in the art. Non-limiting examples include but are not limited to mice bearing mutated SOD1 protein. The mutation may be G93A (mSOD1$^{G93A}$), or G85R (mSOD1$^{G85R}$). Assays showing binding of such mutated and misfolded protein can be performed in vitro, such as exemplified herein below.

ALS is a fatal neurodegenerative disease caused by degeneration of the upper and lower motor neurons. ALS patients and animal models of inherited ALS, like mutant Cu/Zn superoxide dismutase (mSOD1), display similar inflammatory responses at the site of the motor neuron injury, enabling both the CNS resident and systemic inflammatory cells to balance between neuroprotection and neurotoxicity.

By quantitation of inflammatory signaling molecules, as well as the presence/absence of immune cells, the regression or progression of the disease can be indicated, for example, so as to determine treatment efficacy.

Non-limiting example of inflammatory signaling molecules includes cytokines. Specific cytokines which are elevated in ALS patients include, but are not limited to, TNF-α, TNFR1, IL1β, IL-6, IL-8, and VEGF. Detection and/or determination of such cytokines can be performed using immune-assays, including, but not limited to enzyme-linked immunosorbent assay (ELISA), as would be apparent to one of ordinary skill in the art.

ALS progression is known to be attributed, in part, to cytotoxic microglia cells, which activate antibody-dependent cell-mediated cytotoxicity (ADCC) leading to neuron damage. Therefore, determining the presence, level, or both, of cytotoxic microglia cells in the CNS, can indicate treatment efficacy. Determining the presence and/or level of microglia cells can be performed by any method known in the art, and may include immuno-assays, such as flow cytometry (e.g., FACS), and immunohistochemistry using anti-active microglia cell biomarkers, e.g., Nox2, TNF-α, IL-10, IL-α, $I_{NOS}$, IL-6, MMP-12, and Interferons (INFs).

In some embodiments, the subject suffers from ALS. In some embodiments, the subject is at risk for developing ALS.

In some embodiments, the method further comprises administering to the subject the pharmaceutical composition of the invention. In some embodiments, the method further comprises administering to the subject the pharmaceutical composition of the invention when the detected misfolded SOD1 is above a predetermined threshold.

According to some embodiments, the method is for reducing the amount of misfolded SOD1 aggregates. In some embodiments, the method is for clearing misfolded SOD1 aggregates. In some embodiments, the method is for reducing any one of the numbers of SOD1 aggregates, size or SOD1 aggregates, or both.

Screening Methods

According to some embodiments, there is provided a method of screening for a compound suitable for treating, ameliorating, preventing or inhibiting the progression of ALS, comprising contacting a misfolded SOD1 with a compound, and determining the amount of antibody bound to the misfolded SOD1 in the presence of the compound, wherein reduction of the amount of antibody bound to the misfolded SOD1 in the presence of the compound compared to the amount of antibody bound to the misfolded SOD1 in the absence of the compound, indicates the compound is suitable for treating, ameliorating, preventing or inhibiting the progression of ALS, wherein the antibody is the antibody of the invention.

In some embodiments, the compound is a small molecule.

The terms "reduce" and "inhibit" are used herein interchangeably, and encompass a reduction of at least 5%, at least 15%, at least 25%, at least 40%, at least 50%, at least 75%, at least 85%, at least 100%, or any range or value therebetween, compared to a baseline. In some embodiments, reduce is by 1-10%, 5-20%, 15-35%, 30-60%, 50-75%, 70-95%, or 90-100% compared to a baseline. Each possibility represents a separate embodiment, of the invention.

As used herein, the term "baseline" encompasses a naïve or untreated state. For clarity, a non-limiting example for a baseline would be comparing an experimentally treated group compared to a non-treated group.

As used herein, the term "about" when combined with a value refers to plus and minus 10% of the reference value. For example, a length of about 1,000 nanometers (nm) refers to a length of 1,000±100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Example 1

The inventors have recently employed an innovative computational approach to map surface areas of misfolded SOD1 that are predisposed to aberrant protein-protein interactions (PPI). The analysis enabled the identification of the structural motive, namely β6/β7 loop (the Greek Key loop), which is hypothesized to mediate the initiation of SOD1 aggregation and prion-like propagation of the misfolding signal among structurally intact SOD1 molecules.

To their hypothesis that the putative β6/β7 loop epitope becomes exposed upon SOD1 misfolding, the inventors used a β6/β7 loop-derived peptide (SE-21-Am: EDSVIS-LSGDHCIIGRT-Amide [17aa]) as a keyhole limpet hemocyanin (KLH)-conjugated (using glutaraldehyde method for conjugation via —NH2 group) immunogen to generate a rat monoclonal antibody (anti-β6/β7-loop mAb) against this region (named 6D12B10). The anti-β6/β7-loop mAb exhibited a complete discrimination between the intact $SOD1^{WT}$ and misfolded familial ALS (fALS) mutants of SOD1 ($SOD1^{MUT}$, e.g., $SOD1^{G93A}$ and $SOD1^{G85R}$) (FIG. 1B). Moreover, anti-β6/β7-loop mAb recognized metal-free apo-$SOD1^{WT}$ as misfolded protein similar to $SOD1^{G93A}$ and $SOD1^{G85R}$. The saturation of apo-$SOD1^{WT}$ with metals ($Cu^{2+}$ and $Zn^{2+}$) by dialysis, to produce holo-$SOD1^{WT}$, completely abolished mAbs binding, indicating that the conformational change associated with the exposure of the β6/β7 loop epitope is coupled to the metal loss and is entirely reversible. These results strongly supported the inventors' hypothesis that the putative noxious β6/β7 loop epitope is concealed in the intact SOD1 and becomes exposed upon misfolding. The loss of stabilizing metals, especially $Zn^{2+}$ is considered as the primary event which triggers the noxious structural transformation of SOD1, ultimately resulting in amyloid aggregation. Therefore, it is possible that the exposure of the β6/β7 loop epitope represents an early manifestation of the SOD1 noxious misfolding, and it is a common feature for both $SOD1^{WT}$ and fALS $SOD1^{MUT}$. This early β6/β7 loop epitope is fundamentally different from the late epitopes of misfolded SOD1 such as those exposed on the dimer interface upon SOD1 monomerization; they correspond to the advanced stages of SOD1 misfolding and are apparently irreversible.

Importantly, in terms of the epitope's precise location, 6D12B10 mAb recognized the (SED ID NO: 11)
EDSVISLSGDHCIIGRT peptide (SE-21) and did not recognize the overlapping (SEQ ID NO: 13)
LSGDHCIIGRTLVVHEK peptide (SE-12) (overlapped region is underlined), suggesting the epitope is located in the N-terminal-middle portion of SE-21 peptide.

Because of the existence of ALS-linked secretory pathways for SOD1, immunization has been proposed as a potential treatment strategy for ALS. However, active and passive immunizations of ALS mice using misfolded SOD1 as antigen and antibodies raised against it, respectively, were only marginally effective in delaying disease onset and progression. One possible explanation for the failure of immunization could be the inability of the antibodies to discriminate and subsequently block the disease-mediating epitope(s) on misfolded SOD1. The results indicated that the aggregation-initiation β6/β7 loop region represents a unique epitope, whose blocking might be effective in preventing the initial steps of the amyloid formation and propagation of the noxious misfolding signal.

The inventors conclude that by blocking this early epitope, the primary steps of the amyloid formation and propagation of the misfolding signal (and thus disease onset and/or progression) can be attenuated.

Example 2

Targeting SOD1 β6/β7 Loop Epitope Using a mAb in an ALS Model

Blocking the β6/β7 loop epitope by mAbs may prevent the early steps of amyloid formation and attenuate/halt the spreading of the misfolding signal and disease progression. A single-chain antibody comprising the fragments of the mAb variable regions is constructed. The advantages of such antibody are its small size, low immunogenicity and the ability to be used in a gene delivery system, such as recombinant adeno-associated virus (AAV), for intra- or extracellular expression. The AAV vector is intravenously or intrathecally injected directly into the cerebral spinal fluid (CSF). Presymptomatic and symptomatic ALS mice over-expressing different levels of SOD1$^{MUT}$ (e.g., G93A [high] and G37R [low]) are administrated with the virus and the therapeutic modality of the mAb, i.e., its effect on disease onset and/or progression is evaluated.

Example 3

High-Throughput Screening of Misfolded SOD1 Small-Molecule Inhibitors

The ability of the β6/β7 loop-targeted mAbs to recognize the primary misfolding event in SOD1, can be utilized in a high throughput (HTS; such as an ELISA-based format) to identify small-molecule compounds capable of mimicking metal ions ($Zn^{2+}$ and $Cu^{2+}$) in their ability to stabilize the SOD1 structure in its native conformation (as in holo-SOD1$^{WT}$). A compound that binds into the surface cavity shaped by the two parallel β6/β7 loops in the native dimer (FIG. 1A) is expected to stabilize the native dimer conformation and prevent both the exposure of the putative noxious β6/β7 loop epitope and the engagement of the cavity by a similar epitope from another misfolded SOD1 molecule. A library of drug-like compounds available from the Israeli National Center of Personalized Medicine or from other commercial sources to identify compounds that prevent mAb binding to apo-SOD1$^{WT}$ or to SOD$^{MUT}$s (e.g., G93A and G37R) will be screened. In addition, the well-defined structure of the surface pocket (FIG. 1A) enables to formulate a three-dimensional pharmacophore description to be used in a virtual screen of libraries of commercially available compounds using docking software. Selected hits are evaluated in cellular and animal ALS models, and are expected to alleviate amyloid formation by SOD1, interfere with aberrant PPI and attenuate/halt the disease progression by preventing the recruitment of new SOD1 molecules into the noxious pool.

Example 4

Improving the Affinity of β6/β7 Loop-Targeted mAb by Directed Evolution

Improving the mAb pharmacodynamics properties will be attempted by optimizing its affinity to the target using a yeast surface display (YSD) directed evolution methodology that takes advantage of the chaperone-assisted folding, disulfide bond formation, and the quality control mechanisms of the eukaryotic secretory pathway. One of the benefits of YSD over other protein engineering technologies is that multi-color fluorescence activated cell sorting (FACS) screening enables normalization of binding signal by protein expression level, thus can quantitatively discriminate between clones that differ by as little as twofold in binding affinity to the desired target. Libraries of mAb variants bearing mutations in the CDR regions are constructed and screened using a positive selection for improved affinity to a misfolded SOD1 target and a negative selection to prevent interactions with the intact SOD1 protein. Improved clones are evaluated in ALS animal models, as above.

Example 5

Single Chain Fv-Ab Selectively Recognizes Misfolded SOD1 Variants

Figure 2:
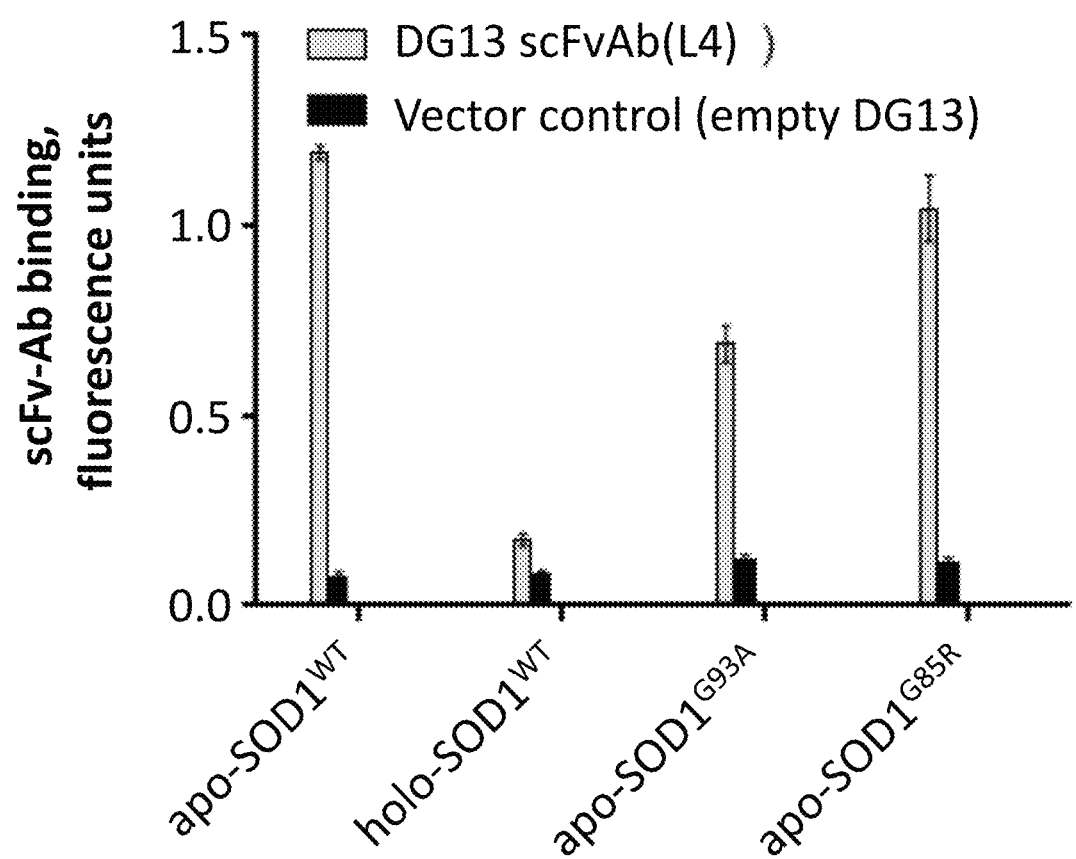
FIG. 2 is a vertical bar graph showing that the scFv-Ab selectively recognizes misfolded SOD1 variants (WT and mutants), similarly to the antibody of the invention. Binding of secreted scFv-Ab (as supernatant of HEK 293 cells transfected with the vector expressing scFv-Ab) to SOD1 variant (apo-SOD1$^{WT}$, holo-SOD1$^{WT}$, apo-SOD1$^{G93A}$, and apo-SOD1$^{G85R}$), was quantified by enzyme-linked immunosorbent assay (ELISA).

The inventors have constructed a single-chain fragment variable antibody (scFv-mAb), representing a hybrid protein that comprises both heavy and light chain variable Ig regions of the anti-β6/β7-loop mAb connected by a short flexible linker (linker length 15-20 amino acids). The advantages of single-chain antibody are its small size, low immunogenicity and increased half-life (due to the reduced clearance via Fc-mediated microglia phagocytosis), and the ability to be used in a gene delivery system, such as recombinant adeno-associated virus, AAV6, for intra- or extracellular expression. AAV vectors have a broad cell type tropism, provide stable and safe gene expression and minimize immune response. When injected into CSF (intrathecally), AAV vectors have been shown to confer sustained protein expression throughout the CNS, including spinal cord and motor neurons. Recent advances in AAV vector engineering enabled these vectors (AAV9) to be injected directly IV to obtain efficient CNS expression DNA sequences encoding the scFv-Ab of the invention were further optimized in terms of the codon usage for expression in mammalian cells (e.g., murine). To confirm the functionality of the scFv-mAb, the inventors have subcloned it into an expression vector under the control of a CMV promoter, linked to an immunoglobulin (Ig) k-secretory signal, and a c-myc epitope for subsequent detection. The expression and secretion of a properly folded and functional scFv-mAb was tested in transfected HEK293 cells by ELISA using misfolded SOD1 as antigen and anti-c-myc antibody for detection (FIG. 2). Following the in vitro functional evaluation, an AAV vector encoding for a secretable scFv-mAb protein (AAV-scFv-mAb) was constructed and used for in vivo studies employing ALS animal models.

Example 6

Therapeutic Modality of the scFv-mAb

To evaluate the therapeutic modality of the scFv-mAb, i.e., its effect on disease onset and/or progression, presymptomatic and symptomatic mice (both genders) transgenic for G93A fALS SOD1 mutant (SOD1$^{G93A}$), which is characterized by high level of transgene expression, and as a result, fast disease onset (~90 d) and progression (end-stage ~150 d), are injected intrathecally with the AAV-scFv-mAb of the invention. By varying the age (disease stage) of the mice at the time of vector administration, the contribution of the β6/β7 loop epitope to different stages of ALS pathogenesis, such as disease onset or progression, can be elucidated. If vector administration to the symptomatic animals slows down the disease progression, then the scFv-mAb is used for the treatment of ALS patients. If the scFv-mAb is effective when administered to presymptomatic mice, but not to symptomatic mice, then the scFv-mAb is used for prophylactic purposes in known carriers of fALS SOD1 mutations.

scFv-mAb is evaluate, as part of a follow-up research, in an ALS mouse model of SOD1$^{G37R}$, which expresses a considerably lower level of the transgene as compared to SOD1$^{G93A}$ mice, resulting in delayed disease onset (~240 d)

and slow progression (end-stage ~420 d). To evaluate scFv-mAb expression in the nervous tissue, spinal cord sections are examined by immunostaining using an anti-myc Ab. Control cohorts are injected with AAV-GFP, and both experimental groups are followed and analyzed for behavior, disease onset and progression, survival, pathology, and viral distribution. The treated mice are monitored for disease onset and progression using weekly body weight and hind limb grip strength measurements. Survival curves of the groups are compared to establish any effect on disease onset and progression. Survival is defined by the inability of mice to right themselves 30 seconds after being placed on their sides (at which point the mice is sacrificed). In addition, an ALS scoring system to quantify the decline of motor functions as the disease progresses is used to assess the effect of the vector administration on ALS phenotype: normal with no sign of motor dysfunction (4 points); hind limb tremors when suspended by the tail (3 pts); gait abnormalities (2 pts); dragging of at least one hind limb (1 pts); inability to right itself within 30 s (0 pts). The motor neuron degeneration is analyzed histochemically in the lumbar ventral horn spinal cord sections using antibodies against specific motor neuron markers, such as HB9 (MNX1), ISL-1, CHAT or SMI32; and acid fuchsin to detect degenerating acidophilic neurons. Motor neuron death in ALS is accompanied by neuroinflammatory processes characterized by the activation of astrocytes and microglia. The levels of inflammatory markers in the lumbar spinal cord are assessed immunohistochemically by using antibodies against the markers of activated microglia (Iba1) and astrogliosis (GFAP). To assess the effect of the AAV-scFv-mAb administration on the loads of misfolded SOD1, total spinal cord lysates are analyzed by immunoprecipitation using a mAbs specific for misfolded SOD1.

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An antibody or an antigen-binding portion thereof, the antibody comprising three heavy chain CDRs (CDR-H) and three light chain CDRs (CDR-L), wherein: CDR-H1 comprises the amino acid sequence set forth in SEQ ID NO: 1 (DSAIH), CDR-H2 comprises the amino acid sequence as set forth in SEQ ID NO: 2 (WINTYTGKPTYADDFKG), CDR-H3 comprises the amino acid sequence as set forth in SEQ ID NO: 3 (SVYSYDGTFYRYFLDA), CDR-L1 comprises the amino acid sequence as set forth in SEQ ID NO: 4 (RASESVSKHIH), CDR-L2 comprises the amino acid sequence as set forth in SEQ ID NO: 5 (LASSLES), and CDR-L3 comprises the amino acid sequence as set forth in SEQ ID NO: 6 (QQSWNDPWT).

2. The antibody or antigen-binding portion thereof of claim 1, comprising a heavy chain comprising the amino acid sequence of SEQ ID NO: 7.

3. The antibody or antigen-binding portion thereof of claim 1, comprising a light chain comprising the amino acid sequence of SEQ ID NO: 9.

4. The antibody or an antigen-binding portion thereof of claim 1, wherein the antigen binding fragment is selected from the group consisting of a Fv, Fab, F(ab')$_2$, scFv or a scFv$_2$ fragment.

5. The antibody or antigen-binding portion thereof of claim 1, having specific binding affinity for misfolded SOD1.

6. The antibody or antigen-binding portion thereof of claim 1, having specific binding affinity for the amino acid sequence set forth in SEQ ID NO: 11 (EDSVISLSGDHCII-GRT).

7. The antibody or antigen-binding portion thereof of claim 1, wherein said antibody or antigen-binding portion thereof is humanized.

8. A recombinant adeno-associated virus (AAV) vector comprising one or more polynucleotide sequences encoding the antibody or an antigen-binding portion thereof of claim 1.

9. A pharmaceutical composition comprising the antibody or an antigen-binding portion thereof of claim 1, a recombinant AAV vector comprising one or more polynucleotide sequences encoding the antibody or an antigen-binding portion thereof of claim 1, or a combination thereof, and a pharmaceutically acceptable carrier.

10. A method for treating amyotrophic lateral sclerosis (ALS) in a subject in need thereof, comprising administering to said subject a therapeutically effective amount of:
  i. the antibody or an antigen-binding portion thereof of claim 1;
  ii. a recombinant AAV vector comprising one or more polynucleotide sequences encoding the antibody or an antigen-binding portion thereof of claim 1;
  iii. a pharmaceutical composition comprising (i), (ii), or both, or any combination thereof.

11. The method of claim 10, further comprising a step of selecting a subject having increased misfolded SOD1 levels compared to control, wherein said selecting said subject comprises:
  i. providing a sample of bodily fluid from said subject;
  ii. contacting said bodily fluid with said antibody or antigen-binding fragment thereof; and
  iii. determining the levels of said antibody or antigen-binding fragment thereof bound to misfolded SOD1 compared to control.

12. The method of claim 10, wherein said antibody or antigen-binding portion thereof binds to the amino acid sequence set forth in SEQ ID NO: 11 of said subject.

13. The method of claim 12, wherein said antibody or antigen-binding portion thereof blocks a misfolded SOD1, blocks said amino acid sequence set forth in SEQ ID NO: 11, or blocks both.

14. The method of claim 10, wherein said antibody or antigen-binding portion thereof prevents or reduces the rate of oligomerization or aggregation of said misfolded SOD1 in said subject.

15. The method of claim 14, wherein said rate of oligomerization or aggregation of said misfolded SOD1 is prevented or reduced in the serum or a tissue of said subject, and optionally wherein said tissue is selected from the group consisting of muscle tissue and neural tissue.

16. A method of in vitro detecting misfolded SOD1 in a subject, comprising:
  i. providing a sample of bodily fluid from said subject;
  ii. contacting said bodily fluid with the antibody or antigen-binding fragment thereof of claim 1; and
  iii. detecting said antibody or antigen-binding fragment thereof bound to misfolded SOD1, thereby detecting misfolded SOD1 in said subject.

17. The method of claim 16, wherein said subject is afflicted by ALS.

* * * * *